United States Patent [19]

Jaggers et al.

[11] 3,947,574

[45] Mar. 30, 1976

[54] SOLID STERILIZING COMPOSITIONS

[75] Inventors: Brian George Jaggers, Romford; Keith Frederick Ufton, Ilford; Horst Richard Wagner, Ongar, all of England

[73] Assignee: Bush Boake Allen Limited, London, England

[22] Filed: June 29, 1971

[21] Appl. No.: 158,047

[30] Foreign Application Priority Data

July 1, 1970 United Kingdom............... 31864/70

[52] U.S. Cl. ................ 424/127; 252/522; 424/128; 424/149; 424/249; 424/287
[51] Int. Cl.² A01N 9/00; A01N 11/00; A61K 7/46; C11B 9/00
[58] Field of Search .......... 424/343, 346, 128, 149, 424/287, 127, 249; 260/429.3; 252/186, 187, 522

[56] References Cited
UNITED STATES PATENTS

| | | | |
|---|---|---|---|
| 2,187,821 | 1/1940 | Nelles | 260/429.5 |
| 2,681,922 | 6/1954 | Balthis | 260/429.3 |
| 3,098,861 | 7/1963 | Russell | 260/429.5 |

*Primary Examiner*—Sam Rosen
*Assistant Examiner*—D. W. Robinson
*Attorney, Agent, or Firm*—Herbert H. Goodman

[57] ABSTRACT

Sterilising composition comprising a chemical reactive compound with a perfumery alcohol or phenol such as bleaching, scouring, chemical cleansing and sanitary sterilising, e.g. mobile toilet, compositions are perfumed by the incorporation therein of one or more monomeric or oligomeric titanium or zirconium esters of a perfumery alcohol or phenol. Preferred esters are monomeric titanate esters of formula $Ti(OR)_4$ where R is the residue of a perfumery alcohol or phenol. Said oligomers are prepared by hydrolysis of a monomeric titanate or zirconate ester with from 50 to 90 moles water per 100 moles monomeric ester. Said sterilising compositions provide controlled release of perfume by hydrolysis of said esters during use and exhibit reduced degradation of said perfumery alcohol or phenol during storage.

15 Claims, No Drawings

SOLID STERILIZING COMPOSITIONS

This invention relates to solid sterilising compositions used for cleansing or sanitary purposes such as bleaches, scouring compositions comprising chemical cleansing agents and sanitary sterilising compositions as used, for example, in mobile toilets.

Such compositions invariably comprise reactive chemicals such as hypochlorites, chlorocyanurates, chlorinated trisodium polyphosphate solid peroxidic agents, alkalis such as caustic soda or acidic materials such as the "Nitrecake" sanitary compositions. Where, as is normally the case, the compositions are required to be perfumed the presence of these reactive chemicals imposes a limitation on the range of perfumery chemicals which may be used. Perfumery alcohols and phenols in particular tend to be degraded by the aforesaid chemicals especially by caustic soda as normally used in mobile toilets.

Our co-pending applications Ser. Nos. 158,048 and 158,049 filed of even date herewith disclose the use in solid washing compositions of, respectively, monomeric and oligomeric titanate and zirconate esters of perfumery alcohols and phenols. These materials have low volatility and may be retained in solid washing compositions almost indefinitely under anhydrous conditions. On coming into contact with water they hydrolyse, liberating the perfumery alcohol or phenol, at a rate dependent upon the temperature, pH, quantity of water and the chemical nature of the ester. The aforesaid monomeric esters have the formula $MA_4$, where M is titanium or zirconium and the groups A are the same or different organic groups, at least one of which is a group of the formula [— O — R], where R is the residue of a perfumery alcohol or phenol. The aforesaid oligomeric esters have the formula

where M and A are as hereinbefore defined and $n$ is an integer and are prepared by reaction of a monomeric ester $MA_4$ with from 50 to 90 moles preferably 50 to 80 moles, most preferably 50 to 60 moles of water per 100 moles monomeric ester.

We have now discovered that these monomeric and oligomeric titanate and zirconate esters of perfumery alcohols and phenols may be used in the aforesaid sterilising compositions to retain the perfumery alcohol or phenol structure almost indefinitely without degradation under anhydrous conditions. On coming into contact with water, as will occur when the compositions are put to use, the perfume is liberated to perform its required function.

Accordingly, the invention provides solid sterilising compositions comprising a chemical reactive with perfumery alcohols or phenols and a titanium or zirconium compound containing one or more groups of the formula M—O—R, where M is titanium or zirconium and R is the residue of a perfumery alcohol or phenol.

The novel sterilising compositions may be any such as mentioned above comprising a reactive chemical used as a sterilising agent, chlorine or oxygen releasing cleansing agents such as hypochlorites, chlorocyanurates, chlorinated phosphate derivatives such as chlorinated trisodium polyphosphate, highly basic chemicals such as lime or caustic alkalis or acidic materials such as used in the well known "nitre cake" compositions. The invention is particularly applicable to those compositions comprising caustic alkalis, especially caustic soda.

The titanium or zirconium compound may be any such as described in our aforesaid copending Applications having the formula

where $m$ is zero or an integer, M is titanium or zirconium and the groups A are the same or different organic groups, at least one of which is a group [— O — R], where R is the residue of a perfumery alcohol or phenol. The perfumery alcohol or phenol may be any odoriferous mono or polyhydric alcohol or phenol used or suggested for use in perfumery compositions, for example such as described in the books 'Synthetic Perfumes' by West, Strausz and Barton, published by Arnold & Co. (London) 1969, 'Soap, Perfumery and Cosmetics', 7th Edition by W. A. Poucher, published by Chapman & Hall (London), 1959 and 'Perfume and Flavour Chemicals' by Steffen Arctander, published by the author (Montclair) 1969. In particular, possible such compounds include linalol, $\beta$-phenyl ethyl alcohol; benzyl alcohol; menthol; n hexanol, $\alpha$-terpineol; eugenol; cis - hex - 3 - en - 1 - ol; n-nonanol; citronellol; n-decanol; geraniol; nerol; myrcenol; dihydrocitronellol; dihydrolinalol; dihydrogeraniol; isoborneol; pelargol or 2, 6 - dimethyloctan - 8 - ol; farnesol, dihydrofarnesol, nerolidol, $\alpha$-phenyl - n - propyl alcohol; -phenyl - n - butyl alcohol; -phenyl - n - amyl alcohol; cinnamyl alcohol; phenylethylene glycol; anisyl alcohol; odoriferous carbinols, such as dimethyl benzyl carbinol; phenylethyldimethyl carbinol; methylphenyl carbinol; dimethylphenylcarbinol; trichloromethyl phenylcarbinol, ethylbenzylcarbinol, methylbenzylcarbinol, isopropylbenzyl carbinol, ethyl - n - amylcarbinol, methyl - n - amyl-carbinol, $\omega$- hydroxymethyllongifolene, carbinols obtainable by reaction of limonene with formaldehyde (see W. German O L S No. 19, 37, 017) such as 6 and 10 hydroxymethyl - 1, 8 - p - methadiene, and 8 - camphene carbinol (as described in West German O L S No. 19, 36, 209) 2 - hydroxy - $\gamma$-pinene; verbenol; carveol; 2 - hydroxy - 6 - p - menthene; 5 - hydroxy - 3 - p - menthene; 3 - hydroxy -2,5 - dimethyl - 1,4, 6 - octatriene; 6,8 - dihydroxy - 1 - p - menthene; 1 - hydroxy - 2 - p - menthene; 4 - hydroxy - 2 - p- menthene; piperitol; carvitol; 3 - hydroxy - 1,1,2,3 -tetramethyl - 4 - cyclohexene; 3 - hydroxy - 2 - methyl - 6 - methylene - 1,7-octadiene, 1-hydroxy - 2 - methylene - 2,7 -octadiene, 3 - hydroxy - 2 - dimethyl - 1,7 octadiene and 1 -hydroxy - 2,6 - dimethyl - 2,6 - octadiene. Zirconate and titanate esters of residues of hydrocyacids corresponding to perfumery lactones may also be used; such perfumery lactones include ambrettolide; exaltolide and dihydroambrettolide.

Phenol esters of titanates and zirconates which may be used in the compositions of the invention include those of vanillin; eugenol; ethylvanillin, homovanillin; isoeugenol; methyl-iso-eugenol; benzyl-iso-eugenol; thymol and p-tert-butylphenol.

Most preferably all groups A in the titanate or zirconate esters are of the formula [O — R] but where two groups A are to be non-perfumery groups they may also be comprised in the same molecule of a difunctional compound such as diol a hydroxy-acid or an alkylolamine such as triethanolamine. Such difunctional derivatives are generally less readily hydrolysed than derivatives of monofunctional organic groups. Alkylolamines and hydroxy-acids such as lactric acid also often form 6 co-ordinate chelated compounds with titanium and zirconium which further decreases the ease of hydrolysis. Diols which may be used include (2-methylpentane-2, 4-diol); 2-ethyl-hexane - 1,3 - diol and hexane 1,6 diol.

The titanate or zirconate compounds may be either monomers or oligomers, according to whether m in the aforesaid general formula is zero or an integer. With oligomers it is preferred that they be mixtures formed by hydrolysis of from a monomeric ester of formula $MA_4$ with from 50 to 90, more preferably 50 to 80 most preferably 50–60 moles water per 100 moles monomeric ester. Monomers are preferred over oligomers.

Titanium compounds are preferred to zirconium as being cheaper.

A titanate or zirconate ester for any particular use will be chosen with regard to the perfumery qualities of the alcohol or phenol, and the ease of hydrolysis and possibly the physical character, of the ester. Ease of hydrolysis generally decreases with increasing size of ester, phenol residues are also generally less readily hydrolysed than alcohol ones. Increasing degrees of polymerisation of the esters also reduce the susceptibility to hydrolysis, the most marked difference being between monomers and dimers. With monomers in which not all of the groups R are perfumery alcohol or phenol groups the choice of the other substituents will also effect the ease of liberation of the perfume due to the general property of orthotitanates that on hydrolysis the first two substituents to be hydrolysed are removed far more readily than the second two. Thus a mixed orthotitante comprising two perfumery alcohol or phenol substituents together with two difficultly hydrolysable substituents, e.g. a diol such as mentioned above, will tend to liberate perfume on hydrolysis more readily than will a mixed ester comprising two perfumery alcohol or phenol substituents together with two nonperfumery substituents which are more readily hydrolysed.

The esters may either be liquid or solid. Oligomers are generally solid. Monomeric orthotitanate alcohol esters are generally liquid where the substituents contain not more than about 10 to 12 carbon atoms; esters with larger substituent groups are normally solid. In most cases phenol esters are either solids or very high boiling liquids.

Besides the aforesaid titanate and zirconate esters the novel compositions will normally contain other known perfumery compounds which do not chemically interact with the titanates or zirconates and the odours of which harmonize to form a perfumery blend. In general both the titanate and zirconate oligomers will be compatible with most of the diversity of materials known to perfumers in compounding perfumery compositions according to well-established principles, e.g. materials such as described in the books 'Synthetic Perfumes', by West Strausz and Barton; published by Arnold and Co. (London) 1969 and 'Soap, Perfumery and Cosmetics', Vol II, 7th Edition, by Poucher, published by Chapman & Hall Ltd. (London), 1959, and 'Perfume and Flavour Chemicals' by Steffen Arctander published by the author (Montclair USA) 1969.

The titanate and zirconate esters for use according to the invention may be prepared by known means, e.g. by reaction of titanium tetrachloride with excess alcohol or phenol. Removal of hydrogen chloride liberated by the reaction is necessary in order to effect substitution greater than disubstitution and this may be done either by conducting the reaction in the presence of metallic sodium or by passing anhydrous ammonia through the reaction mixture. After reaction unreacted alcohol or phenol may be removed from the mixture by distillation, if necessary under reduced pressure. The titanium or zirconium ester product may be purified by distillation if desired. The esters may also readily be prepared from tetra-esters by alcohol or phenol interchange using stoichiometric quantities of alcohol and preferably starting from the ester of the lower boiling alcohol which latter may be removed by distillation as the reaction proceeds. Tetra (n-butyl) titanate is often a convenient starting material. Mixed esters containing residues of both perfumery and non-perfumery alcohols or phenols or esters containing residues of different perfumery alcohols or phenols may be prepared by the same means. Orthotitanates or zirconates may also be reacted with carboxylic acids, hydroxycarboxylic acids or other chelating agents such as alkylolamines in similar fashion to give esters containing both perfumery and non-perfumery substituents. In all such cases reactions are conveniently conducted by concurrent removal of displaced alcohol.

The mixed oligomeric esters may be prepared by hydrolysis of the monomeric titanate or zirconate esters using from 50 to 90, more preferably 50 to 80, most preferably 50 to 60, moles water per 100 moles monomeric ester. The hydrolysis may be effected by simply adding the predetermined quantity of water to a known quantity of a monomeric titanate or zirconate ester ($MA_4$) and subsequently recovering an oligomeric mixture from the product. Where the oligomeric mixture is a solid it will be formed in the reaction product as a precipitate which may be filtered off. Otherwise the liberated alcohol may be distilled off, preferably under reduced pressure, to leave a liquid oligomeric mixture product although it may be desirable to leave any liberated perfumery alcohol in the product to enhance its odour characteristcs. Preferably the hydrolysis is carried out in the presence of an inert, watermiscible organic solvent such as dioxane.

We are uncertain of the nature of the oligomeric mixtures obtainable by any given hydrolysis. The obvious reaction scheme might be expected to be according to the equations (for hydrolysis of a monomer $M(OR)_4$):

$$M(OR)_4 + H_2O \rightarrow M(OR)_3OH + ROM$$
$$M(OR)_3OH + M(OR)_4 \rightarrow (RO)_3M\text{—}O\text{—}M(OR)_3 + ROH$$
<div style="text-align:center">dimer</div>

$$(RO)_3M\text{—}O\text{—}M(OR)_3 + H_2O \rightarrow (RO)_3M\text{—}O\text{—}M(OR)_2OH + ROH$$
$$(RO)_3M\text{—}O\text{—}M(OR)_2OH + M(OR)_4 \rightarrow (RO)_3\text{—}M\text{—}O\text{—}M(OR)_2\text{—}OH(OR)_3 + ROH$$
<div style="text-align:center">trimer</div> and so on. In the general case of hydrolysis of a monomer $MA_3OR$ the reaction would be expected to stop at the dimer stage if the groups A were not hydrolysable. With a monomer $(M(OR)_4$ a whole series of oligomers and polymers up to the ultimate formation of the oxide $MO_2$ would be possible. However we believe that the reactions occurring are actually far more complicated than the above scheme suggests. For example reaction of a titanium monomeric ester $Ti(OR)_4$ with water in a 2:1 molar ratio appears to yield a trimer and not a dimer as the above equations would predict. We have in fact been unable to detect any dimeric material in the reaction product.

By using as a starting material an orthotitanate or orthozicronate ester of two or more perfumery alcohols or phenols, or by subjecting a mixture of two or more ortho esters of different perfumery alcohols or phenols to controlled hydrolysis it is also possible to obtain a mixed oligomer containing different perfumery groups with varying susceptibilities to hydrolysis.

The quantity of titanium or zirconium compound employed in the novel sterilising compositions may vary widely depending upon the nature of the composition, the nature of the perfumery alcohol or phenol from which the titanium or zirconium compound derives and upon the nature of any other perfumery materials in the composition. Thus a sanitary sterilising composition will normally comprise from 0.2 to 20% more usually 0.5 to 10% by weight of a compounded perfumery composition, whereas a scouring powder will generally comprise from 0.05 to 1%, more usually 0.1 to 0.5% by weight of compounded perfumery composition. In the present application, where, as will usually be so, the titanium or zirconium compound is used as an ingredient of a compounded perfumery composition that composition may consist largely or predominantly of the titanium or zirconium compound if the latter is employed primarily on account of the perfumery note of the derived alcohol or phenol ROH or the composition may comprise relatively small amounts of the titanium or zirconium compound where the latter is used on account of its fixative effect on other perfumery materials.

In the general case, therefore, the titanium or zirconium compound will be used as part of a compounded perfumery composition of which it comprises from 1 to 98% by weight, more usually 2 to 70% by weight. The compounded perfumery composition itself may represent from 0.05 to 10% more usually 0.05 to 5%, say 0.1 to 5% by weight of the sterilising composition. Where the titanium or zirconium compound is used alone and not as part of a compounded perfumery composition it will generally be used in quantities of from 0.05 to 10% more usually 0.05 to 5%, say 0.1 to 5% by weight in the sterilising composition.

The novel compositions may be compounded by any appropriate known methods of mixing. Normally the titanate or zirconate ester will be used in conjunction with other perfumery compounds and the sterilising composition will be prepared by admixture of all the perfumery components in the form of a compounded perfumery composition to the other ingredients of the sterlising composition.

The invention is illustrated by the following Examples wherein all parts are by weight.

EXAMPLE I

A perfumery foundation was prepared incorporating a number of orthotitanate esters of perfumery alcohols prepared by reaction of 1:4 molar ratio of tetra-butyl titanate with the respective perfumery alcohols by removal of butanol. The foundation had the following composition:

| | |
|---|---|
| Tetra Cinnamyl Titanate | 30 |
| Tetra Linalyl Titanate | 30 |
| Tetra Citronellyl Titanate | 40 |
| Tetra Terpinyl Titanate | 50 |
| Tetra Geranyl Titanate | 180 |
| Tetra Phenyl Ethyl Titanate | 200 |
| | 530 |
| Phenyl Ethyl Iso Butyrate | 5 |
| Benzyl Acetate | 10 |
| Cedarwood Oil | 10 |
| Citronella Oil | 10 |
| Clove Stem Oil | 10 |
| Musk Xylene | 10 |
| Phenyl Acetaldehyde Di Methyl Acetal | 10 |
| Phenyl Ethyl Acetate | 10 |
| Amyl Cinnamic Aldehyde | 20 |
| Diphenyl Oxide | 20 |
| Gamma Undecalactone 10% in Di Ethyl Phthalate | 20 |
| Iso butyl Phenyl Acetate | 20 |
| Trichloro Methyl Phenyl Carbinyl Acetate | 20 |
| Benzyl Benzoate | 40 |
| Methyl Resinate | 45 |
| Benzyl Alcohol | 60 |
| Ethylene Glycol mono Phenyl Ether | 150 |
| | 1000 |

Quantities of from 0.1 – 1% by weight of this foundation were then thoroughly mixed into an unperfumed base of a standard solid proprietary scouring powder as sold for domestic use, incorporating hypochlorite bleach and peroxide agents. The aromas of the titanate-esterified perfumery alcohols were only appreciable on contacting the thus perfumed scouring powder with water.

EXAMPLE II

To proprietary cleansers comprising "nitre cake" perfumed with from 0.1 to 2.5 of a standard pine-type perfumery foundation were admixed amounts of from 50 to 250% by weight on the quantity of the pine-type perfume of a mixture comprising the following ingredients:

| | |
|---|---|
| Borneol | 50 |
| Linalyl Titanate Oligomers | 50 |
| Nerolin Bromelia | 150 |
| Terpinyl Titanate Oligomers | 750 |
| | 1000 |

The linalyl and terpinyl titanate oligomers were prepared by addition to ortholinalyl titanate and orthoterpinyl titanate, prepared as described above, of 50 moles water per 100 moles monomeric ester. The water was added to the orthoesters in stoppered flasks which were well shaken and then stood overnight after which the oligomers formed precipitated as solids and were filtered off.

The thus perfumed toilet cleanser showed no appreciable linalol or terpinol perfumery note until water was added.

EXAMPLE III

A compounded perfumery composition was prepared containing the following ingredients:

| | |
|---|---|
| Diphenyl Oxide | 10 |
| Trichloro Methyl Phenyl Carbinyl Acetate | 20 |
| Phenyl Ethyl Phenyl Acetate | 20 |
| Phenyl Acetaldehyde Di Methyl Acetal | 20 |
| Tetra (Para Tert Butyl Cyclo Hexyl) Titanate | 30 |
| Tetra Citronellyl Titanate | 120 |
| Tetra Phenyl Ethyl Titanate | 330 |
| Tetra (Tetra Hydro Geranyl) Titanate | 450 |
| | 1000 |

The titanate esters were prepared by a method analogous to that of Example I. This composition was found to be suitable for blending into the base of nitre cake type sanitary sterilising compositions in quantities of from 0.5 to 5.0% by weight on the sterilising compositions to give perfumed products in which there was a negligible tendency of the titanate-esterified alcohols to degrade.

EXAMPLE IV

A compounded perfumery composition was prepared from the following ingredients:

| | |
|---|---|
| Borneol | 50 |
| Terpinolene | 150 |
| Pine Oil American | 300 |
| Tetra Phenyl Ethyl Titanate | 100 |
| Tetra Linalyl Titanate | 100 |
| Tetra Terpinyl Titanate | 300 |
| | 1000 |

The titanate esters were prepared by a method analogous to that of Example I. This composition was found to be suitable for blending into caustic soda based mobile toilet compositions in quantities of from 1 to 5% by weight on the toilet compositions to give perfumed products in which there was a negligible tendency of the titanate - esterified alcohols to degrade.

We claim:

1. A perfumed solid sterilizing composition comprising at least one sterilizing component selected from the group consisting of hypochlorites, chlorocyanurates, chlorinated phosphates, caustic alkalis, lime and niter cake and containing as a perfumery component at least one perfumery component selected from the group consisting of
   i. a perfumery monomeric titanium and zirconium esters of the formula $M(OR)_4$; and
   ii. perfumery oligomeric titanium and zirconium esters of the formula $(RO)_3M(O—M (OR)_2)_nOR$ prepared by reaction of a monomeric titanium or zirconium ester of formula $M(OR)_4$ with from 50 to 90 moles water per 100 moles monomeric ester and subsequent recovery of said oligomeric ester from the resulting reaction mixture,
   wherein M is titanium or zirconium; $n$ is an integer and R is the residue of a perfumery alcohol or phenol ROH, said perfumery alcohol or phenol is selected from the group consisting of linalol; β-phenyl ethyl alcohol; benzyl alcohol; menthol; n-hexanol, α-terpineol; eugenol; cis-hex-3-en-1-ol; n-nonanol; citronellol; n-decanol; geraniol; nerol; mercenol; dihydrocitronellol; dihydrolinalol; dihydrogeraniol; isoborneol; 2,6-dimethyloctan-8-ol; farnesol; dihydrofarnesol; nerolidol; α-phenyl-n-propyl alcohol; γ-phenyl-n-butyl alcohol; γ-phenyl-n-amyl alcohol; cinnamyl alcohol; phenylethylene glycol; anisyl alcohol; dimethyl-benzyl carbinol; phenylethyldimethyl carbinol; methylphenyl carbinol; dimethylphenylcarbinol; trichloromethyl phenylcarbinol; ethylbenzylcarbinol; methylbenzylcarbinol; isopropylbenzyl carbinol; ethyl-n-amylcarbinol; methyl-n-amyl-carbinol; ω-hydroxymethyllongifolene; 6-and 10-hydroxymethyl-1,8-p-methadiene; 8-camphene carbinol; 2-hydroxy-γ-pinene; verbenol; carveol; 2-hydroxy-6-p-menthene; 5-hydroxy-3-p-menthene; 3-hydroxy-2,5-dimethyl-1,4,6-octatriene; 6,8-dihydroxy1-p-menthene; 1-hydroxy-2-p-menthene; 4-hydroxy-2-p-menthene; piperitol; carvitol; 3-hydroxy-1,1,2,3-tetramethyl-4-cyclohexene; 3-hydroxy-2-methyl-6-methylene-1,7-octadiene; 1-hydroxy-2-methylene-2,7-octadiene; 3-hydroxy-2-dimethyl-1,7 octadiene; 1-hydroxy-2,6-dimethyl-2,6-octadiene; ambrettolide; exaltolide; dihydroambrettolide; vanillin; eugenol; ethylvanillin; homovanillin; isoeugenol; methyl-isoeugenol; benzyl-iso-eugenol; thymol; and p-tertbutylphenol.

2. The perfumed sterilizing composition according to claim 1 wherein said perfumery component is at least one compound selected from the group consisting of tetracinnamyl titanate, tetralinalyl titanate, tetracitronellyl titanate, tetraterpinyl titanate, tetrageranyl titanate, tetraphenylethyl titanate, tetra-(para-tert-butylcyclohexyl) titanate, tetra-(tetra-hydrogeranyl) titanate, linalyl titanate oligomers, and terpinyl titanate oligomers.

3. The perfumed sterilizing composition according to claim 2 which also contains at least one perfumery component other than said tetratitanium esters and said titanate oligomers; and wherein said tetratitanate esters and titanate oligomers are from 1–98% by weight of the total weight of perfumery components in said perfumed sterilizing composition.

4. The perfumed sterilizing composition according to claim 1 which also contains at least one perfumery component other than said monomeric titanium and zirconium esters and said oligomeric titanium and zirconium esters; and wherein said titanium and zirconium esters and oligomeric titanium and zirconium esters are from 1–98% by weight of the total weight of perfumery components in said perfumed sterilizing composition.

5. The perfumed sterilizing composition according to claim 4 wherein said titanium and zirconium esters and oligomeric titanium and zirconium esters are from 2–70% of the total weight of perfumery components in said perfumed sterilizing composition and wherein said total perfumery components are from 0.05–10% by weight of said perfumed sterilizing composition.

6. A perfumed solid sterilizing composition consisting essentially of niter cake and from 0.05–10% by weight of a compounded perfumery composition comprising from 1–98% by weight of at least one monomeric titanium ester of formula $Ti(OR)_4$, wherein R is the residue of a perfumery alcohol or phenol selected from the group consisting of linalol; β-phenyl ethyl alcohol; benzyl alcohol; menthol; n-hexanol; α-terpineol; eugenol; cis-hex-3-en-1-ol; n-nonanol; citronellol; n-decanol; geraniol; nerol; myrcenol; dihydrocitronellol; dihydrolinalol; dihydrogeraniol; isoborneol; 2,6-dimethyloctan-8-ol; farnesol; dihydrofarnesol; nerolidol; α-phenyl-n-propyl alcohol; γ-phenyl-n-butyl alcohol; γ-phenyl-n-amyl alcohol; cinnamyl alcohol; phenylethylene glycol; anisyl alcohol; dimethylbenzyl carbinol; phenylethyldimethyl carbinol; methylphenyl carbinol; dimethylphenylcarbinol; trichloromethyl phenylcarbinol; ethylbenzylcarbinol; methylbenzylcarbinol; isopropylbenzylcarbinol; ethyl-n-amylcarbinol; methyl-n-amyl-carbinol; ω-hydroxymethyllongifolene; 6-and 10-hydroxymethyl-1,8-p-methadiene; 8camphene carbinol; 2-hydroxy-γ-pinene; verbenol; carveol; 2-hydroxy-6-p-menthene; 5-hydroxy-3-p-menthene; 3-hydroxy-2,5-dimethyl-1,4,6-octatriene; 6,8-1-dihydroxy-1-p-menthene; 1-hydroxy-2-p-menthene; 4-hydroxy-2-p-menthene; piperitol; carvitol; 3-hydroxy-1,1,2,3-tetramethyl-4-cyclohexene; 3-hydroxy-2-methyl-6-methylene-1,7-octadiene; 1-hydroxy-2-methylene-2,7-octadiene; 3-hydroxy-2-dimethyl-1,7-octadiene; 1-hydroxy-2,6-dimethyl-2,6-octadiene; ambrettolide; exaltolide; dihydroambrettolide; vanillin; eugenol; ethylvanillin; homovanillin; isoeugenol; methyl-isoeugenol; benzyl-iso-eugenol; thymol; and p-tertbutylphenol.

7. The perfumed sterilizing composition according to claim 6 wherein said compounded perfumery composition comprises from 0.1–5% by weight of said perfumed sterilizing composition; and wherein said monomeric titanium ester is from 2–70% by weight of said total perfumery components in said perfumed sterilizing composition.

8. The perfumed sterilizing composition according to claim 7 wherein said titanium ester is tetra-(tetrahydrogeranyl) titanate.

9. The perfumed sterilizing composition according to claim 7 wherein said titanium ester is tetracinnamyl titanate.

10. The perfumed sterilizing composition according to claim 7 wherein said titanium ester is tetralinalyl titanate.

11. The perfumed sterilizing composition according to claim 7 wherein said titanium ester is tetracitronellyl titanate.

12. The perfumed sterilizing composition according to claim 7 wherein said titanium ester is tetraterpinyl titanate.

13. The perfumed sterilizing composition according to claim 7 wherein said titanium ester is tetrageranyl titanate.

14. The perfumed sterilizing composition according to claim 7 wherein said titanium ester is tetraphenylethyl titanate.

15. The perfumed sterilizing composition according to claim 7 wherein said titanium ester is tetra-(para-tertbutyl-cyclohexyl) titanate.

* * * * *

UNITED STATES PATENT AND TRADEMARK OFFICE
CERTIFICATE OF CORRECTION

PATENT NO. : 3,947,574
DATED : March 30, 1976
INVENTOR(S) : BRIAN GEORGE JAGGERS et al It is certified that error appears in the above-identified patent and that said Letters Patent are hereby corrected as shown below:

Column 3, line 5, correct the spelling of "lactic".

Column 5, line 16, correct the spelling of "orthozirconate".

Column 9, line 7, replace "6,8-1 -dihy-" with --6,8-dihy- --.

Signed and Sealed this

Twentieth Day of July 1976

[SEAL]

Attest:

RUTH C. MASON
Attesting Officer

C. MARSHALL DANN
Commissioner of Patents and Trademarks